United States Patent [19]
Oettel et al.

[11] Patent Number: 5,855,905
[45] Date of Patent: Jan. 5, 1999

[54] COMPOUND PREPARATION FOR THE TREATMENT OF HYPOGONADAL MEN AND MEN WITH HYPOPHYSEAL DISEASES

[75] Inventors: Michael Oettel, Jena; Siegfried Golbs, Leipzig; Michael Dittgen; Carsten Timpe, both of Apolda; Thomas Gräser, Erfurt; Doris Hübler, Schmieden, all of Germany

[73] Assignee: Jenapharm GmbH & Co. KG, Jena, Germany

[21] Appl. No.: 841,719

[22] Filed: Apr. 30, 1997

[30] Foreign Application Priority Data

May 4, 1996 [DE] Germany ......................... 196 19 045.2

[51] Int. Cl.$^6$ .................................................. A61K 13/02
[52] U.S. Cl. .......................... 424/426; 424/422; 424/423; 424/430; 424/434; 424/435; 424/436; 424/464
[58] Field of Search ..................................... 424/422, 423, 424/426, 430, 434–6, 464

[56] References Cited

U.S. PATENT DOCUMENTS

| | | | |
|---|---|---|---|
| 3,863,008 | 1/1975 | Grant ........................................ | 424/177 |
| 4,071,623 | 1/1978 | van der Vies ............................ | 424/238 |
| 4,147,783 | 4/1979 | van der Vies ............................ | 424/243 |
| 4,210,644 | 7/1980 | Ewing et al. ............................. | 424/239 |
| 4,220,599 | 9/1980 | van der Vies ............................ | 260/397.4 |
| 4,473,564 | 9/1984 | de Winter et al. ....................... | 424/238 |
| 5,340,586 | 8/1994 | Pike et al. ................................ | 424/426 |
| 5,639,743 | 6/1997 | Kaswan et al. ........................... | 514/171 |

FOREIGN PATENT DOCUMENTS

| | | |
|---|---|---|
| 2508615 | 9/1975 | Germany . |
| 2624025 | 12/1976 | Germany . |
| 9416709 | 8/1994 | WIPO . |

OTHER PUBLICATIONS

"Testosterone Secretion and Metabolism in Male Senescence," A. Vermeulen et al. *JCE & M.* vol. 34, Aug. 2, 1971, pp. 730–735.
"The influence of pharmaceutical compounds on male fertility," F. Neumann et al. *Medline* Journal Article (1976) 1 page.
"Anabolic–Androgenic Steroids", Kochakian, Charles D. (Ed.), Handbook of Experimental Pharmacology, vol. 43, Heffter–Heubner, New Series, (1976), pp. 430–436.
"Endocrinological Studies with (7∝,17∝)–17–Hydroxy–7–methyl–19–norpregn–5(10)–en–20–yn–3–one(Org OD 14)," J. de Visser et al. *Arzneim.–Forsch./Drug Res.* 34 (II), Nr. 9 (1984) pp. 1010–1017.
"Somatomedin–C Levels in Healthy Young and Old Men: Relationship to Peak and 24–Hour Integrated Levels of Growth Hormone," James R. Florini et al. *Journal of Gerontology*, vol. 40, No. 1,2–7 (1985) pp. 2–7.
"Growth Hormone, Body Composition, and Aging," Daniel Rudman, MD *Journal of the American Geriatrics Society*, vol. 33, No. 11 (Nov. 1985) pp. 800–807.

"Traitement androgénique percutané des hypogonadismes masculins. Efficacité comparée de la testostérone et de la dihydrotestostérone: étude de 40 observations," J.M. Kuhn et al. *Contraception–fertilité–sexualité* –vol. 14, No. 11. (1986) pp. 1031–1036.
"Remington's Pharmaceutical Sciences Handbook", Gennaro,Alfonso R., Mack Publsihing, 18ed, (1990), pp. 1449–1450, 1519–1544, 1602–1614, 1633–1665, and 1682–1691.
"Clinical Review 24 Androgens in the Aging Male," A. Vermeulen *Journal of Clinical Endocrinology and Metabolism*. vol. 73, No. 2, (1991) pp. 221–224.
"Determinants of Sex Hormone Levels in Men as Useful Indices in Hormone–Related Disorders," Ikuko Kato et al.*J. Clin Epidemiol*. vol. 45, No. 12 (1992) pp. 1417–1421.
"Effects of Testosterone Supplementation in the Aging Male," Joyce S. Tenover *Journal of Clinical Endocrinology and Metabolism*, vol. 75, No. 4, (1992) pp. 1092–1098.
"Serum pituitary and sex steroid hormone levels in the etiology of prostatic cancer —a population–based case–control study," S.O. Andersson et al. *Br. J. Cancer*, vol. 68 (1993) pp. 97–102.
"Transdermal Dihydrotestosterone Treatment of 'Andropause,'" Bruno de Lignieres *Annals of Medicine*, vol 25 (1993) pp. 235–241.
"Black–White Comparisons of 20–Year Coronary Heart Disease Mortality in the Evans County Heart Study," Curtis G. Hames et al. *Cardiology*, vol. 82, (1993) pp. 122–136.

(List continued on next page.)

*Primary Examiner*—Thurman K. Page
*Assistant Examiner*—Kathryne E. Shelborne
*Attorney, Agent, or Firm*—Webb Ziesenheim Bruening Logsdon Orkin & Hanson, P.C.

[57] ABSTRACT

A compound preparation for the treatment of hypogonadal men and men with hypophyseal diseases. This invention relates to compound preparations containing biogenous or synthetic androgens and biogenous or synthetic estrogens that are used for the treatment of imbalances of the testosterone metabolism in old age, of hypogonadal men, and of men with hypophyseal diseases. These compound preparations are present in various galenic formulations such as ointments, gels, sprays, TTS systems, tablets, lozenges, capsules, and suppositories. These preparations are used to treat the fluctuations of the testosterone metabolism occurring in old age and with certain diseases such as hypophyseal diseases (adenoma), hypogonadism and/or metabolic syndrome, to maintain the balance between androgens and estrogens found in young and healthy men in ill and/or elderly men as well. The preparations for treating these imbalances are suitable for oral, parenteral, percutaneous, sublingual or rectal administration depending on their galenic form. Thus, unphysiological changes in steroid-converting enzymes such as aromatases and reductases are avoided, which considerably improves the outcome of the therapy.

8 Claims, No Drawings

OTHER PUBLICATIONS

"Endogenous Sex Hormones and Ischemic Heart Disease in Men," J.W.G. Yarnell et al. *Arteriosclerosis and Thrombosis*, vol. 13, No. 4, Apr. 1993, pp. 517–520.

"The Role of Stroke Attack Rate and Case Fatality in the Decline of Stroke Mortality," Paul G. McGovern, Ph.D. et al., *AEP*, vol. 3, No. 5, Sep. 1993, pp. 483–487.

"Male Menopause, Myth or Menace?" S. Mitchell Harman, M.D., Ph.D. et al. *The Endocrinologist*, vol. 4, No. 3, (1994) pp. 212–217.

"17β–Oestradiol counteracts the formation of the more acidic isoforms of follicle–stimulating hormone and luteinizing hormone after menopause," Leif Wide et al. *Clinical Endocrinology*, vol. 40, (1994) pp. 783–789.

"Hormonal Changes in Elderly Men with Non–Insulin–Dependent Diabetes Mellitus and the Hormonal Relationships to Abdominal Adiposity," Tien–Chun Chang et al. *Gerontology*, vol. 40, (1994) pp. 260–267.

"Role of the hypothalamic opioidergic system in the control of gonadotropin secretion in elderly men," N. Mikuma et al. *Andrologia*, vol. 26 (1994) pp. 39–45.

"Pharmakokinetik und Biotransformation von Testosteronenanthat beim Menschen," Dr. M. Hümpel et al. *Schering*, Aug. 5, 1994, pp. 1–13.

"Handbook of Experimental Pharmacology," G.V.R. Born et al. Heffter–Heubner New Series, vol. 43 p. 433 (1985).

"Hagers Handbuch der Pharmazeutischen Praxis 5., vollständig neubearbeitete Auflage", Stoffe E–O, von Bruchhausen, F., pp. 79–82 and 891–892 (1990).

"Hagers Handbuch der Pharmazeutischen Praxis 5., vollständig neubearbeitete Auflage", Stoffe A–D, von Bruchhausen, F., pp. 257–259 (1990).

COMPOUND PREPARATION FOR THE TREATMENT OF HYPOGONADAL MEN AND MEN WITH HYPOPHYSEAL DISEASES

BACKGROUND OF THE INVENTION

1. Field of the Invention

This invention relates to pharmaceutical compound preparations for oral, percutaneous, intranasal, rectal or parenteral application used in the treatment of hypogonadal men with or without metabolic syndrome and of men with hypophyseal diseases.

2. Prior Art

Various endocrine functions undergo changes in the course of the aging process. The insulin-like growth factor (IGF-1) levels in the plasma diminishes in healthy persons as they get older (Rudman D(1985): Growth hormone, body composition, and aging. J Am Geriatr Soc 33: 800–807; Florini JR, Prinz PN, Vitiello MV, Hintz RL (1985): Somatomedin-C levels in healthy young and old men: Relationship to peak and 34-hour integrated levels of growth hormone. J. Gerontol 40: 2–7). The normal aging process in men is accompanied by a hypofunction of the testicles, in particular, by a decline in serum testosterone levels. At the same time, the levels of luteinizing hormone (LH) and follicle-stimulating hormone (FSH) in the plasma are increased (Tien-Chun Chang, Chin-Chia Tung, Yung-Lien Hsiao (1994): Hormonal changes in elderly men with non-insulin-dependent diabetes mellitus and the hormonal relationships to abdominal adiposity. Gerontology 40: 260–267).

The prevalence of specific diseases with or without a disturbed oral glucose tolerance increases parallel to these hormonal changes. Examples of this are the various forms of diabetes mellitus, high blood pressure, hypercholesterolaemia and other disorders of the lipid or lipoprotein metabolism, myocardial infarction, and Alzheimer's disease (Vermeulen A (1991): J. Clin Endocrinol Metab 73: 222). Quite frequently, the so-called metabolic syndrome is found in overweight elderly men which is accompanied by obesity, insulin or insulin receptor resistance, a testosterone deficit and a disproportionately high risk of cardiovascular diseases. There is a considerably increased mortality caused by cerebral or coronary ischaemia (McGovern PG et al. (1993): The role of stroke attack rate and case fatality in the decline of stroke mortality. The Minnesota Heart Survey. Ann Epidemiol. 3: 483–487; Hames CG et al. (1993): Black-white comparisons of 20-year coronary heart disease mortality in the Evans County Heart Study Cardiology 82: 122–136).

Patients with serum-testosterone levels that were regularly below 3.5 ng/ml in repeated tests are commonly called hypogonadal, and they are treated with appropriate androgens in a hormone replacement therapy.

Testosterone replacement may be carried out by oral, intramuscular or transdermal (e. g. transscrotal) application. It should be considered here that the testosterone itself may either become effective in specific target tissues by binding to a specific androgen receptor, or by being aromatized into estradiol or reduced to dihydrotestosterone, the effect of the testosterone therefore mainly depending on the extent of aromatization or reduction. Testosterone acts directly at the androgen receptor in specific organs such as the muscles, the skeleton and the testicles. In various peripheral tissues such as the external genitals, accessory sexual glands (e. g. the prostate) and the skin, however, testosterone has first to be reduced to 5α-dihydrotestosterone to develop its androgenic effect. 5α-dihydrotestosterone is about twice as active as testosterone. In other tissues such as fatty tissue and certain cerebral areas or cells, testosterone is aromatized into the female sex hormone, estradiol, and acts via the estrogen receptor.

3.0 to 10.0 ng/ml of total testosterone, 2% of which (0.06 to 0.2 ng/ml) present as uncombined, "free" testosterone, 0.25 to 0.75 ng/ml as 5α-dihydrotestosterone and <50 pg/ml as 17β-estradiol has been measured in the blood of healthy young men (Ikuko Kato et al. (1992): Determinants of sex hormone levels in men as useful indices in hormone-related disorders. J. Clin Epidemiol. 45:1417–1421; Andersson SO et al. (1993): Serum pituitary and sex steroid hormone levels in the ethiology of prostatic cancer-a population-based case-control study. Br. J. Cancer 68: 97–102; Mikuma N et al. (1994): Role of the hypothalamic opioidergic system in the control of gonadotropin secretion in elderly men. Andrologia 26:39–45).

This well-balanced ratio between the parent substance, testosterone, and its two main metabolites, 17β-estradiol and 5α-dihydrotestosterone is essential for maintaining the physiological equilibrium in males which in turn is responsible for the functioning of the protein, carbohydrate, and lipoprotein metabolisms as well as of the haemopoietic system including fibrinolysis, for the maintenance of the weight of bony and muscular tissue, the functions of the skin and liver, and several behavioural patterns. This illustrates that a disruption to this balance can entail certain states of disease.

Testosterone and estradiol can interact in a very complex way. Estradiol increases the concentration of androgen receptors in certain tissues, thus multiplying the androgenic effect (synergistic effect) while testosterone acts, for example, as an estradiol antagonist in the mammary glands of mice. In addition, androgens in breast cancer cell lines (MCF6 cells) can bind to the estrogen receptor and inhibit the estrogen-dependent progesterone receptor synthesis (antagonistic effect).

The degree to which estrogens are converted and thus the pharmacokinetic profile of the respective androgen can also be influenced by the way in which an androgen molecule is synthetically changed. The orally active 17α-alkylated androgens can only with difficulty, or not at all, be aromatized to estrogens. They lower the levels of HDL cholesterol, $HDL_2$ cholesterol and of the apolipo-proteins, AI and AII. They cause an increase in total and LDL cholesterol, apolipoprotein B, hepatic triglyceride lipase, and lipoprotein lipase levels. Unlike the 17α-alkylated androgens, testosterone esters such as testosterone enanthate only have a minor effect on total and LDL cholesterol levels, though they can cause a minor suppression of HDL cholesterol. This difference between 17α-alkylated and non-alkylated androgens (e. g. testosterone ester) is due to the capability of testosterone or its esters to be aromatized into estrogens. As is generally known, estrogens act contrary to androgens on LDL and HDL cholesterol levels.

In elderly men, however, the metabolic pattern of testosterone changes considerably, i.e. the balance mentioned above of testosterone, 5α-dihydrotestosterone and 17β-estradiol is durably disturbed. This modifies the quantitative aspects of testosterone metabolism: more estrogens and less 5α-reduced metabolites are formed.

Aromatization into estradiol is especially increased in adipose men (De Lignière B (1993) Transdermal dihydrotestosterone treatment of andropause, Ann Med 25: 235–241). If testosterone or its fatty acid ester is applied to hypogonadal men, a much greater portion is aromatized into estradiol than with healthy men. Estradiol levels in the plasma are increased by 70% after percutaneous application (Kuhn JM Laudat MH, Lignières de B, Bricaire H. Lutaon JP (1986) Traitement androgénique percutané des hypogonadismes masculins. Efficacité comparée de la testosterone et de la dihydrotestostérone: étude de 40 observations. Contracept Fert Sex 14: 1031–1036). The estradiol levels in the plasma are even doubled after intramuscular injection (Tenover JS (1992) Effects of testosterone supplementation in the aging male. J. Clin Endocrinol Metab 75: 1092–1098). In many patients, this results in estradiol levels similar to those of women during the follicle phase. It is therefore not astonishing that the application of testosterone to hypogonadal, adipose men may cause a series of unwelcome effects such as triggering or intensification of gynaecomastia and a relative peripheral androgen deficit (decrease in libido, reduced size of the genitals, but also prostatic hyperplasia).

The exogenic supply of testosterone, e. g. of testosterone enanthate, to patients in which gonadal testosterone biosynthesis still works soon reversibly inhibits the endogenic testosterone production for a period of about 2 weeks (H ümpel M. and Oettel M. (1994): Wertende Zusammenfassung Pharmakokinetik und Biotranformation von Testosteronenanthat beim Menschen). This has not been observed after applying estradiol or dihydrotestosterone (DHT) or mesterolone (Oettel M. (1993) in: Hagers Handbuch der Pharmazeutischen Praxis vols. 7 and 8).

Furthermore, the reductive metabolism to the highly androgenic metabolite, 5α-dihydrotestosterone, may be disturbed in old age. Much less androgenic metabolites are formed as the 5β-metabolization pattern is intensified rather than the 5α-metabolic pathway. As a consequence, androgens had to be applied in heavy doses (e. g. 400 to 600 mg testosterone undecanoate/day orally or 200 to 250 mg testosterone enanthate i. m. every 2 to 3 weeks) to achieve the desired androgenic effects. This inevitably increases estradiol levels with the unwelcome side effects mentioned above.

According to Yarnell JWG et al. 1993 (Arterioscl. Thromb. 13: 517–520), estradiol levels in the blood plasma are slightly increased in men with a severe ischaemic heart disease. This Caerphilly Prospective Study involved a total of 2161 healthy control persons aged from 45 to 59 years with estradiol levels in the plasma at 69+/−17 pg/ml (250+/−61 pmol/l), and 134 men of similar age suffering from severe ischaemic heart disease with levels at 71+/−19 pg/ml (257+/−69 pmol/l).

The advantages of estradiol at a low concentration are indispensable, though (as is the case when administering non-aromatizable dihydrotestosterone or one of its derivatives). These advantages include an improvement of cognitive performance, an increase in the level of sex hormone-binding globulin (SHBG), the inhibition of LDL cholesterol oxidation as an important step in atherogenesis, arterial dilatation and the associated improved blood flow through the tissue, and the inhibition of increased gonadotropin and inhibin levels (Harman SM. Blackman MR. (1994) Male menopause, myth or menace? Endocrinologist 4:212–217). Moreover, estradiol seems to prevent age-dependent transformation processes in proteohormones (Wide L. Maessen T. (1994) 17β-Estradiol counteracts the formation of the more acidic isoforms of follicle-stimulating hormone and luteinizing hormone after menopause. Clin Endocronol 40: 783–789).

The efficiency of the unchanged testosterone is also clearly reduced in old age as the most important transport protein, sex hormone-binding globulin (SHBG) binds testosterone much stronger through structural transformation processes. As a result, the portion of free, i.e. biologically active testosterone becomes smaller. 5α-Dihydrotestosterone and estradiol, unlike unchanged testosterone, do not show a significant decrease in old age (Vermeulen A. (1972) Testosterone secretion and metabolism in male senescence. J Clin Endocrinol 34: 730–735).

It is the object of the present invention to provide appropriate pharmaceutical formulations that can prevent the imbalances of testosterone metabolism in old age, in cases of hypophyseal diseases, hypogonadism and/or metabolic syndrome, thereby maintaining the balance of androgens and estradiol known from healthy young men in male senescence as well.

SUMMARY OF THE INVENTION

This object is achieved in accordance with the invention by a compound preparation for the treatment of imbalances of testosterone metabolism in old age, of hypogonadal men and men with hypophyseal diseases, said preparation containing a biogenous or synthetic androgen and a biogenous or synthetic estrogen. The patients are exogenically given the final products of the testosterone metabolism, i.e. a 5α-reduced testosterone/estrogen preparation mixed in a similar or in the same ratio that is natural in young and healthy men.

DETAILED DESCRIPTION OF THE INVENTION

The present invention includes a compound preparation for the treatment of imbalances of testosterone metabolism in old age, of hypogonadal men and men with hypophyseal diseases, said preparation containing a biogenous or synthetic androgen and a biogenous or synthetic estrogen.

The compound preparation of the invention is characterized in that the biogenous androgen contained in it comprises at least one component taken from the group of testosterone, androsterone, androstanolone and other biogenous androgens, or at least one compound that splits off one of the above androgen components shortly after application.

Preferred is a compound preparation according to the invention wherein the biogenous androgen is 5α-dihydrotestosterone or a compound that splits off 5α-dihydrotestosterone shortly after application.

The compound preparation of the invention is further characterized in that the synthetic androgen comprises at least one component from the group of mesterolone, fluoxymesterone, 17-methyl testosterone, and other synthetic androgens, or at least one compound that splits off one of the above androgen components shortly after application.

The compound preparation of the invention is moreover characterized in that the biogenous estrogen comprises at least one component from the group of 17β-estradiol, estrone, estriol, estrane and other biogenous androgens, or at least one compound that splits off one of the above estrogen components shortly after application.

The compound preparation of the invention is further characterized in that the synthetic estrogen comprises at least one component from the group of ethinyl estradiol, mestranol and other synthetic estrogens, or at least one compound that splits off one of the above androgen components shortly after application.

Among the suitable compounds that split off the biogenous or synthetic androgens or the biogenous or synthetic estrogens shortly after application are esters, ethers, amides and salts of the androgens or estrogens with pharmaceutically acceptable acids, alcohols or amines. Suitable acids include mineral acids such as sulfuric acid, hydrochloric acid, phosphoric acid, or organic carboxylic acids containing up to 25 C-atoms such as acetic acid, formic acid, propionic acid, valeric acid, benzoic acid, or fatty acids such as linoleic acid, linolenic acid, oleic acid, myristic acid, undecanoic acid. Suitable alcohols are, for example, aliphatic alcohols containing up to 15 C-atoms such as ethanol, methanol, propanol, or aromatic alcohols such as phenols. Suitable amines are aliphatic amines containing up to 8 C-atoms. α- or β-Amino acids may advantageously be used for esterification, etherification or amide formation. The compounds may be produced in a generally known way.

The object of the invention is achieved in accordance with the invention by combining estrogens and androgens or their derivatives in various forms of preparation or application. In this way, unphysiological changes in steroid-converting enzymes (aromatases, reductases) are prevented, which considerably improves the treatment.

The compound preparation of the invention for the treatment of hypogonadal men with or without a metabolic syndrome and men suffering from hypophyseal diseases consists of fixed combinations of 5α-dihydrotestosterone, its various esters and synthetic derivatives with natural or synthetic estrogens and their various esters and derivatives.

According to the invention, the preferred derivative of dihydrotestosterone is mesterolone.

The natural estrogen of the invention comprises at least one component from the group of 17β-estradiol, estrone, estriol or conjugated estrogens.

The synthetic estrogen of the invention comprises at least one component from the group of ethinyl estradiol or mestranol.

The pharmaceutical preparations may provide this combination in an integrated or in two separate formulations. These can be presentations for oral application such as tablets, capsules and lozenges, presentations for percutaneous application such as transdermal therapeutic systems (TTS) or gels, sprays or ointments, preparations for intranasal applications such as nasal sprays or nose drops, preparations for rectal application such as suppositories, and parenterals such as implants or compacts and ampules.

The preparations are produced in a generally known way using common adjuvants and substrates as described, for example, in "Remington's Pharmaceutical Sciences Handbook, Hack Pub. Co., N. Y., USA".

Suppositories or capsules are alternative presentations of the combination of active agents according to the invention. For this purpose, suppositories and capsules are produced using the common methods and adjuvants.

Furthermore, the preparation of the invention may be applied in the form of a transdermal therapeutic system (TTS). For this purpose, the combinations of active agents according to the invention are incorporated in a TTS in a generally known way. The TTS may be based, for example, on iontophoresis or diffusion or combinations of these two effects, if required. It is attached to the body at an appropriate place. The active ingredients are applied transcutaneously while the rate of application is controlled by the size and active area of the TTS and, optionally, by the voltage applied.

For the preferred oral application, the compound preparations of the invention are best combined in a pharmaceutical pack that contains a presentation containing the daily dose.

Below shall be given a few examples of pharmaceutical presentations of the compound preparation according to the invention:

Mesterolone tablet (25 mg) plus 0.80 mg of estradiol valerate

DHT gel (125 mg/dosi in 2.0 ml) plus 1.0 mg micronized estradiol in the form of a gel Mesterolone tablet (25 mg) plus estradiol patch (0.025 mg of estradiol/day)

DHT enanthate 12.5 mg i.m. and 0.025 mg EV i.m. (as an ampule)

DHT (125 mg) plus estradiol (1 mg) in the form of a spray

Mesterolone tablet (25 mg) plus 0.80 mg of estradiol valerate in the form of a capsule DHT (125 mg) plus 5 mg of estriol in the form of a gel or patch Mesterolone tablet (25 mg) plus 0.50 mg of estradiol valerate in the form of a suppository DHT (125 mg) plus 5 mg of estriol in the form of a nasal spray or nasal drops Mesterolone tablets (25 mg) plus 0.60 mg of conjugated estrogen Other galenic preparations that may be combined in any possible way include, for example:

Biodegradable microspheres, each weighing 300 mg and containing 150 mg of DHT, and releasing a daily dose of 6 mg of DHT combined with:
0.80 mg of estradiol valerate (lozenge, tablet)
estradiol gel (1 mg of micronized estradiol)
estriol gel (5 mg of estriol)
estradiol patches (0.25 mg of estradiol/day)
0.60 mg of conjugated estrogen (lozenge, tablet)

DHT heptanoate 100 mg to 200 mg i. m. combined with:
0.80 mg of estradiol valerate (lozenge, tablet)
estradiol gel (1 mg of micronized estradiol)
estriol gel (5 mg)
estradiol patches (0.25 mg of estradiol/day)
0.60 mg of conjugated estrogen (lozenge, tablet)

EXAMPLE 1

Pharmacokinetic Behaviour of Mesterolone in Combination with Estradiol Valerate (EV)

In a randomized study, the kinetic behaviour of mesterolone (25 mg tablet) in combination with EV (1 mg lozenge) after a single oral application was examined in 24 healthy young male test persons.

Each test person was administered mesterolone and EV after a monitored fasting period of 12 hours. After the application, 18 blood samples were taken from each test person over a period of 60 hours.

The test revealed the following data on the pharmacokinetic behaviour of mesterolone:

| | |
|---|---|
| AUC | 176.8 ng/ml * h |
| $C_{max}$ | 6.9 ng/ml |
| $t_{max}$ | 8.9 h |
| $t_{1/2}$ | 13.2 h |

After 60 hours, the value was down to 0.48 ng/ml, i.e. close to zero.

The following pharmacokinetic data was obtained after analysing estradiol:

|  | free estradiol | free estrone | conjugated estrone |
| --- | --- | --- | --- |
| AUC (pg/ml * h) | 970.8 | 3492.3 | 128701.8 |
| $C_{max}$ (pg/ml) | 38.7 | 164.0 | 15171.0 |
| $t_{max}$ (h) | 7.8 | 7.0 | 2.4 |
| $t_{1/2}$ (h) | 15.9 | 15.7 | 12.5 |

The portion of free estradiol was still at 28 pg/ml after 24 hours.

EXAMPLE 2

Pharmacokinetic Behaviour of Dihydrotestosterone (DHT) in Combination with Estriol Gel In a randomized study, the pharmacokinetic behaviour of DHT and estriol after transdermal application was examined in 18 healthy young male test persons.

The DHT patch contains 150 mg of the active ingredient and was left on the test persons' skin for 24 hours. This galenic form releases 6 mg of DHT per day. The initial values for DHT in the test persons were between 0.43 and 1.24 ng/ml.

The estriol gel contains 5 mg of active ingredient in 0.5 g of gel. This gel formulation was applied one time to 150 $cm^2$ of skin (forearm). All test persons had initial estriol values below the detectable minimum of <3 pg/ml.

For analysis, 12 blood samples were taken from each test person after the application over a period of 48 hours. A Cmax value of 4.51+/−1.23 ng/ml was determined for DHT. The Cmax concentrations for estriol were at 8.82+/−2.54 pg/ml.

A comparison of the findings from the pharmacokinetic studies under Examples 1 and 2 with the findings of a study carried out in healthy young men to whom testosterone enanthate (250 mg i. m.) was applied in combination with an estradiol patch (25 mg), it becomes apparent that high Cmax values of 19.4+/−7.9 ng/ml are reached after 2.4 days for testosterone, and of 148.1+/−26.3 pg/ml for estradiol after 2.7 days. The high estradiol levels determined in this study reflect the late follicle phase in females.

EXAMPLE 3

Clinical Study Carried Out in 23 Hypogonadal Men

This study was carried out on both arms of 23 hypogonadal men whose testosterone level was below 3 ng/ml.

Arm 1 (n=12) 250 mg of testosterone enanthate i. m. every 3 weeks for 12 months

Arm 2 (n=11) 25 mg of mesterolone/day p. o. plus 0.8 mg of estradiol valerate/day p. o. for 12 months The study yielded the following findings:

Arm 1: Testosterone maxima of 22.7+/−14.8 ng/ml were detected in the serum after i. m. application of 250 mg of testosterone enanthate about 2 to 3 days after the respective time of application. The values were still at 6.7+/−2.1 ng/ml after 21 days. Similar results were obtained in subsequent applications. There was no cumulation. When comparing the maximum values with the testosterone levels found in healthy men, a significant increase can be detected, which rules out unwelcome events.

The increased LH levels were reduced in the serum of all participants in the study by inhibiting the endogenous testosterone synthesis still present on a rudimentary scale.

All patients showed an apparent increase in bone density after just 6 months of treatment. All men experienced a pelage increase due to the increased testosterone levels.

Nine out of 12 patients noticed an improvement of the morning erection of their penises. An increase in penis size was detected in 11 men while at the same time the volume of their testicles got smaller.

Symptoms of andropause such as hot flashing, exhaustion, weakness of concentration and reduced efficiency, disgruntlement, disturbances of the libido and potency became less frequent. Nine patients were free of complaints.

The values for the prostate-specific antigen (PSA) were slightly up in all patients. They were between 3.0 and 3.8 ng/ml. An increase in the size of the prostatic glands, however, could not be detected.

Collagen depletion was not detected. All participants in the study showed a thickening of the skin, an increase in water retention, and an improvement of the tension and elasticity of the tissue.

Seven of the 12 patients showed an increased susceptibility to acne after 4 months of treatment. At the same time, the voice pitch of all men lowered towards a bass tone.

Five out of 12 patients developed a gynaecomastia.

Arm 2: After daily administration of mesterolone (25 mg) and estradiol valerate (0.80 mg) to 11 hypogonadal men for a period of 12 months, maximum DHT levels of 5.2+/−2.0 ng/ml were determined 9 hours after an application. Levels of 1.82+/−0.85 ng/ml were still detected after 24 hours. None of the patients receiving a daily dose showed a DHT level below 1.2 ng/ml in the course of the study. Cumulative effects did not occur. The concentrations found can be taken as therapeutically effective levels for the treatment of hypogonadal men.

Maximum estradiol levels of (32.4+/−7.8 pg/ml) were detected 7.9 hours after the first application. This effect repeated after each application while no cumulation was observed. The maximum levels for estrone were at 154.2+/−29.8 pg/ml 6.7 hours after the first application. Again there was no cumulation with estrone.

The estrogen levels found allow the treatment of estrogen-related disorders during andropause. None of the patients showed any more sleep disturbances after 3 months of treatment. Development of acne was not observed in any of the participants in the study because estrogens also inhibit the synthesis of sebum.

As there was no inhibition of LH synthesis, 9 patients showed a slight increase in testosterone levels up to a maximum of 11.3 ng/ml. There was a positive correlation between the testosterone level in the blood and bone mineralization resulting in an increase of bone density in all patients after only 6 months of treatment.

The symptoms of andropause had subsided or vanished in all 11 participants in the study after a maximum of 4 months.

Ten patients showed an increase in penis size and a slight gain in testicle weight. The pelage had also increased in all men.

Prostatic hyperplasia could not be detected in any of the patients after 12 months of treatment.

The combination treatment, unlike testosterone treatment alone, did not result in an increase in PSA; there was no voice change or gynaecomastia.

We claim:

1. A method of treating hyporonadism or hypophyseal disease in a man comprising administering to a hypogonadal man or a man with hypophyseal disease a pharmaceutical preparation containing a biogenous or synthetic androgen and a biogenous or synthetic estrogen.

2. The method according to claim 1 wherein said biogenous androgen comprises at least one component from the group consisting of testosterone, androsterone, androstanolone and other biogenous androgens or at least one compound that splits off one of said androgen components shortly after application.

3. The method according to claim 1 wherein said biogenous androgen is 5α-dihydrotestosterone or a compound that splits off 5α-dihydrotestosterone shortly after application.

4. The method according to claim 1 wherein said synthetic androgen comprises at least one component from the group consisting of mesterolone, fluoxymesterone, 17-methyl testosterone and other synthetic androgens or at least one compound that splits off one of said androgen components shortly after application.

5. The method according to claim 1 wherein said biogenous estrogen comprises at least one component from the group consisting of 17β-estradiol, estrone, estriol, estrane and other biogenous estrogens or at least one compound that splits off one of said estrogen components shortly after application.

6. The method according to claim 1 wherein said synthetic estrogen comprises at least one component from the group consisting of ethinyl estradiol, mestranol and other synthetic estrogens or at least one compound that splits off one of said estrogen components shortly after application.

7. The method according to claim 1 characterized in that said preparation is presented in the form of tablets, capsules, lozenges, transdermal therapy systems, ampules, suppositories, gels, ointments, nasal drops, implants, compacts or biodegradable microspheres.

8. The method according to claim 1 wherein said preparation is suitable for oral, percutaneous, intranasal, rectal, sublingual, transdermal, or parenteral application.

* * * * *

UNITED STATES PATENT AND TRADEMARK OFFICE
CERTIFICATE OF CORRECTION

PATENT NO. : 5,855,905
DATED : January 5, 1999
INVENTOR(S) : Michael Oettel et al.

It is certified that error appears in the above-identified patent and that said Letters Patent is hereby corrected as shown below:

Claim 1 Column 8 Line 66 "hyporonadism" should read --hypogonadism--.

Signed and Sealed this

Eighth Day of June, 1999

Attest:

Q. TODD DICKINSON

*Attesting Officer*   Acting Commissioner of Patents and Trademarks